(12) United States Patent
Hirsch

(10) Patent No.: US 6,475,202 B1
(45) Date of Patent: Nov. 5, 2002

(54) FLEXIBLE AND BREATHABLE ABSORBENT ARTICLES AND THEIR FIXATION TO UNDERGARMENTS

(75) Inventor: Uwe Thomas M. H. Hirsch, Griesheim (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 08/836,558
(22) PCT Filed: Oct. 16, 1995
(86) PCT No.: PCT/US95/13545
§ 371 (c)(1),
(2), (4) Date: May 2, 1997
(87) PCT Pub. No.: WO96/14035
PCT Pub. Date: May 17, 1996

(30) Foreign Application Priority Data

Nov. 5, 1994 (EP) .............................................. 94203231

(51) Int. Cl.⁷ ................................................ A61F 13/15
(52) U.S. Cl. .................................... 604/385.03; 604/389
(58) Field of Search ........................... 604/387, 385.01, 604/385.03, 385.04, 385.05, 386, 389, 390

(56) References Cited

U.S. PATENT DOCUMENTS

| 3,881,489 A | 5/1975 | Hartwell |
| 4,341,216 A | 7/1982 | Obenour |
| 4,758,241 A | 7/1988 | Papajohn .................... 604/387 |

*Primary Examiner*—Dennis Ruhl
(74) *Attorney, Agent, or Firm*—Theodore P. Cummings; Kirsten K. Stone; Kevin C. Johnson

(57) ABSTRACT

The present invention relates to breathable absorbent articles such as sanitary napkins, panty liners, and incontinence pads which are adhered by adhesive to an undergarment during use. More particularly the present invention relates to articles which have an air permeable or breathable back sheet, which have a flexibility in a longitudinal direction, and which are particularly well adhered to the undergarment in order to provide improved comfort to the wearer of the article.

13 Claims, 2 Drawing Sheets

FLEXIBLE AND BREATHABLE ABSORBENT ARTICLES AND THEIR FIXATION TO UNDERGARMENTS

FIELD OF THE INVENTION

The present invention relates to breathable absorbent articles such as sanitary napkins, pantyliners, and incontinence pads which are adhered to an undergarment during use. More particularly the present invention relates to articles which are air permeable or breathable and which have a flexibility in a longitudinal direction which provides improved comfort to the wearer of the article.

BACKGROUND OF THE INVENTION

Disposable absorbent articles such as baby diapers, adult incontinence articles, sanitary napkins and panty liners are well known in the art. These articles have a wearer facing side through which they typically absorb liquids discharged by the wearer. The liquid is stored in an absorbent structure. Liquid leakage from the article through the surface opposite the wearer facing side is usually prevented by incorporating a liquid impermeable backsheet on that side.

It is also well established in the art that a backsheet allowing gaseous fluid (air) communication with the environment, usually referred to as breathability, is highly desirable. Breathability improves with the amount of air permeating through a backsheet. This amount is proportional to the open area (the sum of the area of all apertures) in the backsheet. Obviously too many and particularly too large apertures in the backsheet lead to compromising the liquid leakage prevention, which is the primary function of a backsheet.

Many suggestions how to provide breathable backsheets have been recorded in the art. Numeral attempts of combining the mutual contradicting features of gas permeability and liquid impermeability have been documented in patents and patent applications. However the lack of commercially available breathable disposable absorbent articles indicates that the technology so far suggested has not provided an all around satisfactory result for the desired technical requirements at commercially acceptable conditions. More often than not satisfaction of one desired feature went to such an extreme that the respective other feature was not properly satisfied any longer.

For example sanitary napkins with very high breathability at the cost of frequent liquid leakage (leading to soiling of the undergarments of a wearer) cannot be considered satisfactory. On the other hand satisfying the liquid leakage problem properly usually resulted in almost impermeable, that is non-breathable, backsheets.

Combinations of breathable and liquid permeable sheets in order to provide a certain liquid impermeability while satisfying the desire for breathable backsheets have already been suggested for example in U.S. Pat. No. 3,881,489. In this disclosure a breathable backsheet is provided by confining an outer layer of formed film material having surface aberrations with apertures therein and an inner layer of a paper tissue having a high void volume and having been made hydrophobic by impregnating it with a paraffin wax. This document does not disclose the desire for using a directional liquid transport type polymeric film structure with a hydrophobic fibrous fabric layer made of polymeric material.

Other prior art attempts to provide breathable backsheet assemblies comprising more than one layer are e.g. documented in U.S. Pat. No. 4,341,216, EP-A-109 126 or EP-A-203 821. Neither of these disclosures provides constructions of breathable backsheets similar to the present invention.

Single layer breathable backsheets are known for example from GB-A-2184391, GB-A-2184390, GB-A-2184389, U.S. Pat. Nos. 4,591,523, 4,839,216 or EP 156471. None of the mentioned disclosures attempts however to address the comfort problems associated with stiff or not sufficiently flexible absorbent articles.

Another solution to the problem of conflict between leakage and breathability is of course to provide so much absorbent material that leakage is prevented by liquid retention rather than impermeability of the backsheet. This leads to early designs of catamenial articles having a very thick absorbent core with a fully permeable non-woven or gauze wrapping. However these articles are not used any longer due to being extremely uncomfortable. Also they are too costly due the high material consumption required in order to provide the end user with peace of mind regarding the leakage performance of these articles.

Also this solution, as did other alternatives which increased material consumption, causes the absorbent article to become less flexible. Flexibility in particular the ability to bend and twist easily in longitudinal and preferably in all directions has however become of key importance especially for everyday usage absorbent articles such as panty liners, sanitary napkins and incontinence pads.

Such sanitary napkins, pantyliners, and incontinence pads are typically worn in the crotch region of an undergarment and attached to the undergarment by a so called panty-fastening-adhesive. In order to be comfortable to the wearer these articles need to be flexible. It is believed that the more flexible an absorbent article is the less will it be noticeable to the wearer. Hence this provides comfort by more closely resembling the situation when no such absorbent article is worn.

Flexibility can easily be achieved by reducing the amount of material in an absorbent article or replacing stiff or inflexible components by more flexible ones. However it has long been recognised that extreme flexibility can reduce the absorbent performance of these articles, for example by an insufficient amount of absorbent material or by bunching or densifying of the absorbent material during use. Also a too flexible article may be difficult to handle for the wearer when attaching it to the undergarment.

The problem of too much flexibility in an article due to a low amount of inflexible material has been addressed for example in U.S. Pat. No. 4,217,901 where particularly the stiffness of an absorbent article is increased in order to provide satisfactory performance. This prior art reference accepts the comfort implications caused by its stiffness requirement. Also breathability is not even considered in this document. Therefore flexibility and leakage prevention (as well as breathability and leakage prevention) are mutually apposite characteristics of absorbent articles. Hence flexibility and breathability combined are working in synergy against leakage prevention while all three features are highly desirable.

It now has been found that the comfort of breathable absorbent articles can be drastically improved when providing a high flexibility in longitudinal direction in combination with a particular panty-fastening-adhesive configuration so as to maintain the breathable article flat relative to the undergarment of the wearer. The flexibility then becomes limited only by material requirements (e.g. to provide sufficient absorbent performance) and by handling requirements of the absorbent article.

It is therefore an objective of the present invention to provide sanitary napkins with an improved flexibility without the previously experienced drawbacks. In particular a high degree of flexibility and breathability in the absence of bunching problems without major handling difficulties is achieved by the selected ranges of design parameters of the articles according to the present invention.

It is another objective of the present invention to provide highly flexible absorbent articles in particular sanitary napkins or panty liners having a superior breathability of the backsheet while simultaneously retarding liquid leakage through the backsheet to such an extend that the user of such articles does not experience a recognisable difference between a liquid impermeable backsheet and the breathable backsheet according to the present invention.

These and other objectives of the present invention will be more readily apparent when considered in reference to the following description.

SUMMARY OF THE INVENTION

The present invention provides a breathable absorbent article such as a sanitary napkin, an incontinence pad and particularly a panty liner for use in an undergarment. The absorbent article has a breathable backsheet which comprises a garment facing surface. On the garment facing surface is an adhesive to adhere the article to the undergarment. The article may optionally comprise protective sideflaps which during use are folded around the side edges in the crotch region of the undergarment so as to improve soiling protection for the undergarment. The absorbent article also comprises the other typical components of such articles namely an absorbent core and a liquid pervious wearer facing surface which is preferably provided by a liquid pervious topsheet. The absorbent article comprises a breathable backsheet which usually provides the garment facing surface of the absorbent article. If topsheet and backsheet are present the absorbent core is enclosed by them on the wearer and on the garment side respectively.

The adhesive can be provided across the whole, part or several distinct parts of the garment facing surface. The adhesive is provided so as not to clog the full surface area. If it covers the whole garment facing surface it can be in a filamentary fashion which is random or in a defined design like spirals. The total area of all adhesive on the garment facing surface of the absorbent article defines the actual adhesive surface. In addition a theoretical adhesion surface is given by the periphery of an endless line which is the shortest encircling line of the adhesive without extending beyond the periphery of the garment facing surface itself.

The absorbent article according to the present invention has a surface ratio of theoretical adhesion surface to the garment facing surface in a range of 0.6 to 1, preferably 0.85 to 1 for articles without the protective side flaps and in a range of 0.5 to 1, preferably from 0.7 to 0.9 for articles with protective side flaps. In a preferred embodiment the theoretical adhesion surface is substantially coextensive to the actual surface covered by the adhesive.

In order to realise the benefits of the present invention the absorbent article as a whole needs to provide exceptional flexibility. The flexibility is measured by the modified ASTM method D1388 as described herein below in longitudinal direction. The expression "flexibility" is also referred to as "drapability" due to the particular method. It should be understood that stiffness is characteristic of the opposite behaviour of a material. The flexibility should be in the range of 1300 to 5000, preferably from 2000 to 3500, most preferably 2000 to 3000, mg×cm.

These flexibility values in combination with the surface ratio indicated above provide exceptional wearer comfort without soiling and/or absorbent performance problems due to bunching or densification of the absorbent material and still allows the wearer to attach the article to the undergarment without undue effort. According to the present invention flexibility is measured in longitudinal direction because this is the value more readily measurable and important. In principle the transverse flexibility also could be used, possibly at different values. Due to the small extension of articles in the transverse direction it is however usually not possible to properly measure flexibility in this direction.

The thickness of a preferred embodiment of the present invention especially for pantyliners is less than 3 mm and even more preferably in the range of 0.5 to 1.5 mm according to the thickness measurement method described herein below.

The combination of appropriate panty-fastening adhesive coverage and flexibility is particularly useful in the context of stretchable absorbent articles. Absorbent articles being stretchable in one direction and more so absorbent articles being stretchable in two (or all) directions are inherently flexible. Stretchability in itself already provides an improvement for comfort such that the absorbent articles combining stretchability with the present invention are particularly desirable.

Particularly useful are stretchable absorbent articles having the stretch characteristics described in U.S. application Ser. No. 08/192,240 filed Feb. 4, 1994 and indicated in the Table of FIG. 7 and the respective description of that application.

The second key aspect according to the present invention is the breathability of the backsheet of the absorbent articles. The articles according to the present invention have a breathable backsheet comprising an inner layer and an outer layer where the inner layer is closer to the absorbent core than the outer layer. The outer layer comprises a hydrophobic, gas permeable fibrous fabric layer composed of polymeric fibres such as polymeric non-wovens well known in the art of absorbent articles.

The inner layer comprises a hydrophobic gas-permeable (air-permeable) polymeric film such as a microporous film having micro-apertures or a macroscopically expanded, polymeric film having macro-apertures.

If the inner layer comprises a hydrophobic gas-permeable micro- or macro-apertured, polymeric film, it preferably has a directional liquid transport phenomena. The film has a first and a second liquid transport direction which are opposite to each other. The first liquid transport direction is from the outer layer towards the absorbent core. Liquid transport in the first direction is larger than liquid transport in the second direction when measured under an identical pressure drop across the apertured film.

This directional liquid transport phenomena is preferably provided by funnel shaped apertures with the direction from larger funnel opening towards smaller funnel opening being parallel to the first liquid transport direction.

DETAILED DESCRIPTION OF THE PRESENT INVENTION

Figure 1:
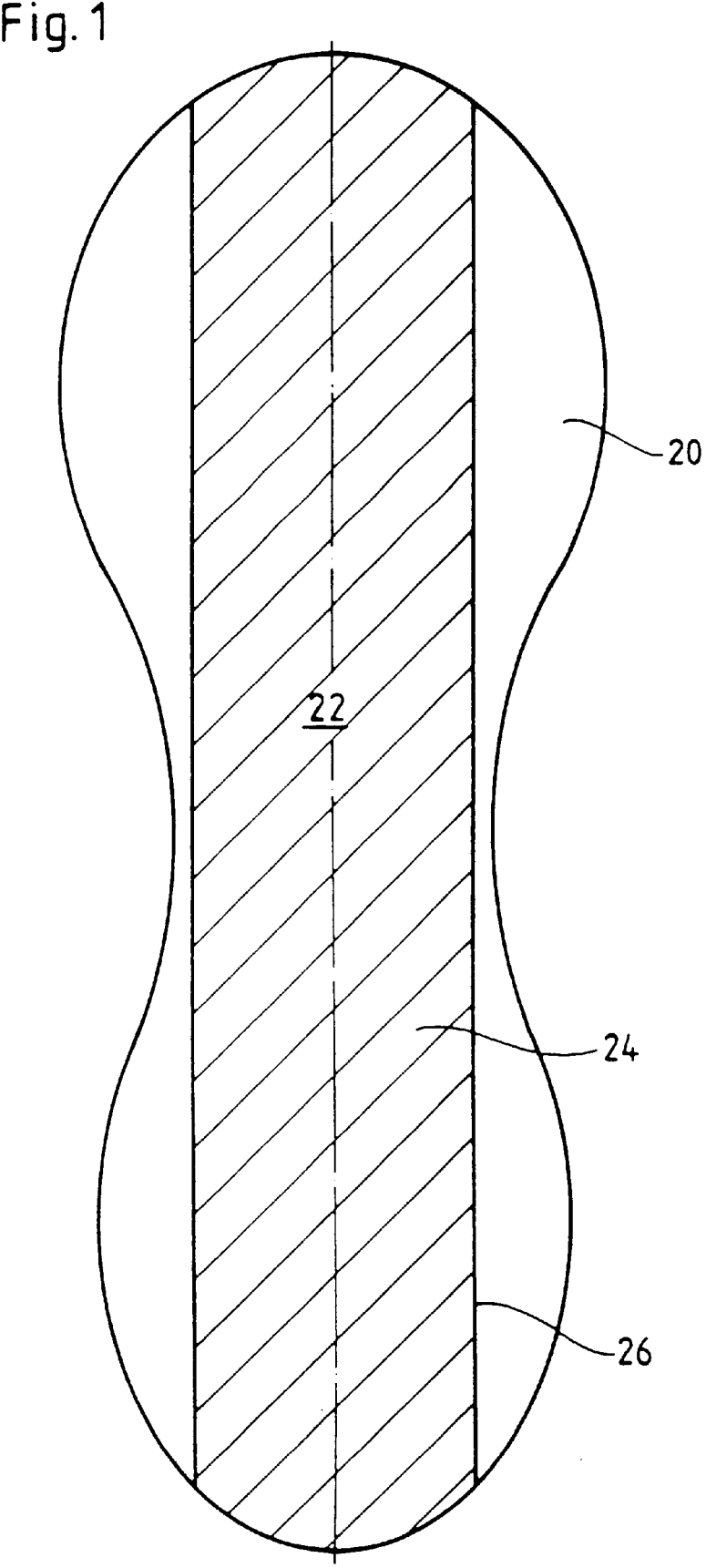
FIG. 1 shows a plan view of the garment facing surface of a pantyliner without protective side flaps according to the present invention.

The present invention will be described by reference to pantyliners. It is however equally well applicable to sanitary napkins or adult incontinence articles which are worn in an undergarment and are joined to the undergarment during wearing of the absorbent article.

Absorbent articles according to the present invention comprise typically three main components: a liquid pervious topsheet, a breathable backsheet and an absorbent core. The absorbent core is enclosed by the backsheet and the topsheet and the article is worn such that the exposed surface of the topsheet faces the wearer of the absorbent article while the exposed surface of the backsheet faces the undergarment to which the article is joined by a panty-fastening attachment means. Typically this is an adhesive but could also be a mechanical attachment.

The present invention is concerned with the flexibility of the article and its breathability. The degree of flexibility is determined by the selection of the materials for the components of the article as mentioned above and their respective quantity. It will be apparent to those skilled in the art that, in order to achieve the flexibility according to the present invention, the selection of kind and quantity of raw materials has to be balanced with other desired characteristics of the absorbent article such as for example absorbent capacity, absorption speed and surface dryness on the outside of the topsheet during use.

Therefore the following description of typical materials of the main components of the absorbent article will allow to provide an almost infinite number of article variants inside and outside the flexibility limitations according to the present invention. Whether or not an absorbent article meets the requirements of flexibility of the present invention can then be confirmed by simple measurements according to the method described below.

The absorbent articles according to a preferred embodiment of the present invention are elastically stretchable. The term "elastically stretchable", as used herein, means that when the stretching forces are removed, the article will tend to return toward its unextended or unstretched (or 'original' dimensions). It need not return all the way to its unstretched dimensions, however. If the absorbent article is elastically stretchable it may be stretchable in one or two directions (which are not-parallel) within the plane of the article i.e. parallel to the garment facing surface.

Materials for elastically stretchable articles can be elastically stretchable per se or be treated so as to provide elastic stretchability. In particular elastic backsheet material, elastic topsheet material, filamentary materials combined with elastic strands, threads or webs as well as shirring, pleating or ring rolling of the materials may be employed in this context. Suitable material and methods are known in the art and e.g. disclosed in detail in U.S. application Ser. No. 08/192240 of Feb. 4, 1994 specifically referred to in order to facilitate selection of materials if stretchable absorbent articles according to the present invention are made.

In the following, non-limiting embodiments of the main elements of the absorbent article are described which can be employed in elastically stretchable or non-stretchable designs.

Absorbent Core

The absorbent core typically includes the following components: (a) optionally a primary fluid distribution layer; (b) optionally, but preferably, a secondary fluid distribution layer; (c) a fluid storage layer; (d) optionally a fibrous ("dusting") layer underlying the storage layer; and (e) other optional components.

a. Primary Fluid Distribution Layer

One optional component of the absorbent cores according to the present invention is the primary fluid distribution layer. This primary distribution layer typically underlies the topsheet and is in fluid communication therewith. The topsheet transfers the acquired menstrual fluid to this primary distribution layer for ultimate distribution to the storage layer. This transfer of fluid through the primary distribution layer occurs not only in the thickness, but also along the length and width directions of the absorbent article.

b. Optional Secondary Fluid Distribution Layer

Also optional but a preferred component of the absorbent cores according to the present invention is a secondary fluid distribution layer. This secondary distribution layer typically underlies the primary distribution layer and is in fluid communication therewith. The purpose of this secondary distribution layer is to readily acquire menstrual fluid from the primary distribution layer and transfer it rapidly to the underlying storage layer. This helps the fluid capacity of the underlying storage layer to be fully utilized.

c. Fluid Storage Layer

Positioned in fluid communication with, and typically underlying the primary or secondary distribution layers, is a fluid storage layer comprising certain absorbent gelling materials and/or other absorbent materials, which can form the carrier matrix for the absorbent gelling materials. Absorbent gelling materials are usually referred to as "hydrogels," "superabsorbent" "hydrocolloid" materials. Absorbent gelling materials are those materials that, upon contact with aqueous fluids, especially aqueous body fluids, imbibes such fluids and thus form hydrogels. These absorbent gelling materials are typically capable of absorbing large quantities of aqueous body fluids, and are further capable of retaining such absorbed fluids under moderate pressures. These absorbent gelling materials are typically in the form of discrete, nonfibrous particles.

The fluid storage layer can comprise solely absorbent gelling materials, or these absorbent gelling materials can be dispersed homogeneously or non-homogeneously in a suitable carrier or it can comprise solely an absorbent carrier material. Suitable carriers include cellulose fibers, in the form of fluff, tissues or paper such as is conventionally utilized in absorbent cores. Modified cellulose fibers such as the stiffened cellulose fibers can also be used. Synthetic fibers can also be used and include those made of cellulose acetate, polyvinyl fluoride, polyvinylidene chloride, acrylics (such as Orlon), polyvinyl acetate, non-soluble polyvinyl alcohol, polyethylene, polypropylene, polyamides (such as nylon), polyesters, bicomponent fibers, tricomponent fibers, mixtures thereof and the like. Preferred synthetic fibers have a thickness of from about 3 denier per filament to about 25 denier per filament, more preferably from about 5 denier per filament to about 16 denier per filament. Also preferably, the fiber surfaces are hydrophilic or are treated to be hydrophilic. The storage layer can also include filler materials, such as Perlite, diatomaceous earth, Vermiculite,. etc., that lower rewet problems.

If dispersed non-homogeneously in a carrier, the storage layer can be locally homogeneous, i.e. have a distribution gradient in one or several directions within the dimensions of the storage layer. Non-homogeneous distribution can also refer to laminates of carriers enclosing absorbent gelling materials partially or fully.

If absorbent gelling materials are present, preferably the storage layer comprises from about 15 to 100% absorbent gelling materials and from 0 to about 85% carrier. Preferably, the storage layer comprises from about 30 to 100%, most preferably from about 60 to 100% absorbent gelling materials and from 0 to about 70%, most preferably from 0 to about 40%, carrier.

Suitable absorbent gelling materials for use herein will most often comprise a substantially water-insoluble, slightly crosslinked, partially neutralized, polymeric gelling material. This material forms a hydrogel upon contact with water. Such polymer materials can be prepared from polymerizable, unsaturated, acid-containing monomers. Suitable unsaturated acidic monomers for use in preparing the polymeric absorbent gelling material used in this invention include those listed in U.S. Pat. No. 4,654,039 and reissued as RE 32,649. Preferred monomers include acrylic acid, methacrylic acid, and 2-acrylamido-2-methyl propane sulfonic acid. Acrylic acid itself is especially preferred for preparation of the polymeric gelling material. The polymeric component formed from the unsaturated, acid-containing monomers can be grafted onto other types of polymer moieties such as starch or cellulose. Polyacrylate grafted starch materials of this type are especially preferred. Preferred polymeric absorbent gelling materials that can be prepared from conventional types of monomers include hydrolyzed acrylonitrile grafted starch, polyacrylate grafted starch, polyacrylates, maleic anhydride-based copolymers and combinations thereof. Especially preferred are the polyacrylates and polyacrylate grafted starch.

While these absorbent gelling materials are typically in particle form, it is also contemplated that the absorbent gelling material can be in the form of macrostructures such as fibers, sheets or strips. These macrostructures are typically prepared by forming the particulate absorbent gelling material into an aggregate, treating the aggregated material with a suitable crosslinking agent, compacting the treated aggregate to density it and form a coherent mass, and then curing the compacted aggregate to cause the crosslinking agent to react with the particulate absorbent gelling material to form a composite, porous absorbent. Such porous, absorbent macro structures are disclosed, for example, in U.S. Pat. No. 5,102,597.

d. Optional Fibrous ("Dusting") Layer

An optional component for inclusion in the absorbent cores according to the present invention is a fibrous layer adjacent to, and typically underlying the storage layer. This underlying fibrous layer is typically referred to as a "dusting" layer since it provides a substrate on which to deposit absorbent gelling material in the storage layer during manufacture of the absorbent core. This layer can comprise all those materials disclosed above as carrier materials for the storage layer. Indeed, in those instances where the absorbent gelling material is in the form of macro structures such as fibers, sheets or strips, this fibrous "dusting" layer need not be included. However, because this "dusting" layer provides some additional fluid-handling capabilities such as rapid wicking of fluid along the length of the pad, its inclusion is typically preferred in absorbent cores according to the present invention.

e. Other Optional Components

The absorbent cores according to the present invention can include other optional components normally present in absorbent webs. For example, a reinforcing scrim can be positioned within the respective layers, or between the respective layers, of the absorbent cores. Such reinforcing scrims should be of such configuration as to not form interfacial barriers to fluid transfer, especially if positioned between the respective layers of the absorbent core. Given the structural integrity that usually occurs as a result of thermal bonding, reinforcing scrims are usually not required for the absorbent structures according to the present invention and indeed may cause the desired flexibility to be unachievable.

Another component which can be included in the absorbent core according to the invention and preferably is provided close to or as part of the primary or secondary fluid distribution layer are odor control agents. Typically active carbon coated with or in addition to other odor control agents, in particular suitable zeolite or clay materials, are optionally incorporated in the absorbent core. These components can be incorporated in any desired form but often are included as discrete, non-fibrous particles.

Topsheet

The topsheet is compliant, soft feeling, and non-irritating to the wearer's skin. As indicated above the topsheet also can be elastically stretchable in one or two directions. Further, the topsheet is fluid pervious permitting fluids (e.g., menses and/or urine) to readily penetrate through its thickness. A suitable topsheet can be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers.

Preferred topsheets for use in the present are selected from high loft nonwoven topsheets and aperture formed film topsheets. Apertured formed films are especially preferred for the topsheet because they are pervious to body exudates and yet non-absorbent and have a reduced tendency to allow fluids to pass back through and rewet the wearer's skin. Thus, the surface of the formed film that is in contact with the body remains dry, thereby reducing body soiling and creating a more comfortable feel for the wearer. Suitable formed films are described in U.S. Pat. Nos. 3,929,135; 4,324,246; 4,342,314; 4,463,045; and 5,006,394. Particularly preferred microapetured formed film topsheets are disclosed in U.S. Pat. Nos. 4,609,518 and 4,629,643. The preferred topsheet for the present invention is the formed film described in one or more of the above patents and marketed on sanitary napkins by The Procter & Gamble Company of Cincinnati, Ohio as "DRI-WEAVE."

Topsheets having not a homogeneous distribution of liquid passage ways but only a portion of the topsheet comprising liquid passage ways are also useful for the present invention. Typically such topsheets would have the liquid passage ways oriented such that they result in a centrally permeable and peripherally impermeable topsheet for liquids.

The body surface of the formed film topsheet can be hydrophilic so as to help liquid to transfer through the topsheet faster than if the body surface was not hydrophilic. In a preferred embodiment, surfactant is incorporated into the polymeric materials of the formed film topsheet.

Alternatively, the body surface of the topsheet can be made hydrophilic by treating it with a surfactant such as is described in the above referenced U.S. Pat. No. 4,950,254.

Breathable Backsheet

The breathable backsheet prevents the exudates absorbed and contained in the absorbent core from wetting articles that contact the sanitary napkin such as pants, pajamas and undergarments. The inner layer of the backsheet is a polymeric film having apertures and the outer layer is a fibrous fabric layer. Both layers are hydrophobic improving their liquid retention characteristics without effecting their breathability.

The fibrous fabric layer of the outer layer preferably has a basis weight of 10 to 100 $g/m^2$, more preferably 15 to 30 $g/m^2$. The fibres can be made of any hydrophobic polymeric material usual in the art of making fibrous fabric layers. Depending on the circumstances of the ultimate use and manufacturing of the breathable absorbent article fibres of polyethylene, polypropylene, polyester, polyacetate or combinations thereof (intra- and inter-fibres combinations) have been found useful. The fibres are preferably spunbonded, carded or melt blown.

The polymeric film can be provided with "micro-porous" apertures or with larger apertures also referred to as "macro-apertures" and is then typically a macroscopically expanded apertured film. The distinction is the visible discernability of the apertures and their ability to retain liquid.

Although the pattern as a whole of micro-apertured surface aberrations of the apertured film in the backsheet of the articles according to the present invention may be visible to the normal naked eye i.e., a normal eye having 20/20 vision unaided by any instrument that changes the apparent size or distance of an object or otherwise alters the visual powers of the eye, when the perpendicular distance between the viewer's eye and the plane of the web is about 300 mm, the micro-apertured surface aberrations comprising the pattern are not individually discernible to the normal naked eye when the perpendicular distance between the viewer's eye and the plane of the web is about 300 mm.

In this regard, the individual micro-apertured surface aberrations of the present invention preferably have a maximum cross-sectional dimension of 500 micro meters or less, more preferably 0.2 micro meters or less, most preferably 0.1 micro meters or less, to satisfy the foregoing individual discernibility criteria.

Typically the apertures in the macroscopically expanded apertured film of the inner layer are larger than about 0.5 mm. It is also possible to have combinations of micro-apertures and macro-apertures. For leakage prevention reasons it is however preferred to have more micro-apertures than macro-apertures.

The apertured film according to the present invention can be any of those well known in the art. This includes in particular, but is not limited to those films disclosed in U.S. Pat. Nos. 3,929,135, 4,151,240, 4,319,868, 4,324,426, 4,342,314, 4,591,523, and 4,609,518, 4,629,643, 5,158,819, 4,772,444.

A preferred apertured film comprised in the inner layer of the breathable backsheet has funnel shaped apertures similar to those described e.g. in U.S. Pat. No. 3,929,135 for large apertures or U.S. Pat. No. 4,629,643 for micro-apertures. The apertures maybe circular or non-circular but have a cross sectional dimension at one end of the funnel which is wider than the opening at the other end of the funnel. The direction from the larger funnel opening towards the smaller opening is of course parallel to the first liquid transport direction. The apertured films can be made of any material typical in the art but preferably is made of a polymer similar to those used for the fibrous fabric layer.

The minimum hydraulic diameter of the apertures in the film should be as small as possible while still providing sufficient gas permeability without hydraulic blockage of the apertures. A hydraulic diameter of as little as 2 to 5 micro meter for micro-apertures and up to 700 micro meters for larger apertures has been found possible in the context of the present invention. Hydraulic diameter for non circular apertures is the diameter that a circular aperture with the same cross section would have. Diameter is always determined in the plane of smallest cross section of an aperture.

In particularly preferred embodiments of the present invention the layers of the breathable backsheet are not joined to each other in the area coextensive with the absorbent core. Particularly inner and outer layers can be thermally laminated or soldered to each other in only some spots for integrity reasons but remain unattached across at least 50% of the area coextensive with the absorbent core.

The novel multilayer breathable backsheets suggested in simultaneously filed applications entitled "Breathable backsheet design for disposable absorbent articles" and "Breathable dual layer backsheet design for disposable absorbent articles" both assigned to The Procter and Gamble Company and designating M. Depner and M. Divo as coinventors disclose particularly useful backsheet embodiments which are also useful in the context of the present invention. However it should be understood that these multi layer backsheet designs are in particular useful to improve flexibility if the addition of layers does not increase stiffness. This can be achieved e.g. by maintaining the amount of material while increasing the number of layers i.e. several lighter/thinner layers replacing a thicker layer.

The Panty-fastening-adhesive

The backsheet typically forms the garment facing surface on which the panty fastening adhesive is placed.

According to the present invention it is important that the ratio of theoretical adhesion surface to actual garment facing surface is within the range according to the claims of the present invention. The theoretical adhesion surface is defined by the surface area inside the shortest possible endless line encircling the panty-fastening adhesive however without extending beyond the periphery of the garment facing surface.

Figure 2:
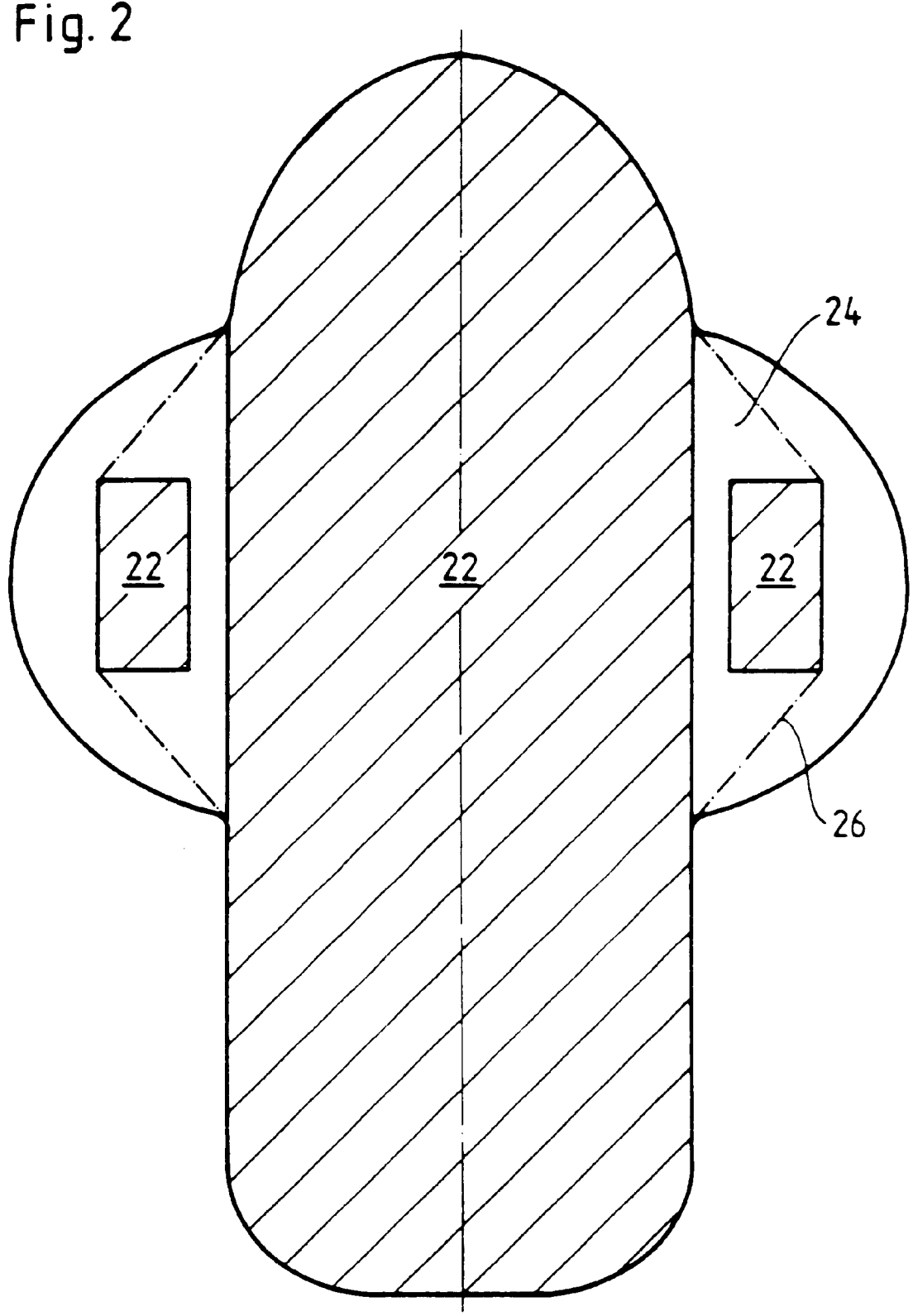
FIG. 2 shows the garment facing surface of a sanitary napkin having protective side flaps according to an alternative embodiment of the present invention.

In addition the ratio of actual adhesive surface to garment facing surface is in the range of 0.2 to 0.8. If there is for example one rectangular adhesive area on the garment facing surface then the theoretical adhesion surface and the actual adhesive surface are identical, this can be seen in FIG. 1 where the adhesive 22 is indicated by hatching. The encircling line 26 results in a theoretical adhesion surface 24 identical to the surface covered by the adhesive 22. For absorbent articles having protective side flaps FIG. 2 shows that the three adhesive areas 22 are smaller in surface area than the theoretical adhesion surface 24 encircled by line 26. If the backsheet is elastically stretchable the adhesive surfaces are measured on the unstretched backsheet prior to initial stretching thereof.

Panty-fastening-adhesives can comprise any adhesive or glue used in the art for such purposes with pressure-sensitive adhesives being preferred. Suitable non-extensible adhesives are Century A-305-IV manufactured by the Century Adhesives Corporation, Instant Lock 34-2823 manufactured by the National Starch Company, 3 Sigma 3153 manufactured by 3 Sigma, and Fuller H-2238ZP manufactured by the H. B. Fuller Co. Suitable adhesive fasteners are also described in U.S. Pat. No. 4,917,697.

In order to maintain to breathability provided by the backsheet according to the present invention it is important that the panty fastening adhesive does not close or clog the apertures in the garment facing side of the backsheet. For this purpose it is possible to use an adhesive in such a pattern to only seal off a fraction of the apertures such that no more than 80% of the actual garment facing surface is covered by adhesive. On the other hand 20% adhesive coverage has been found necessary to provide the benefit of proper attachment to the undergarment of the breathable absorbent article.

Therefore, preferably the panty fastening adhesive is applied in intermittent patterns such as for example intermittent dots, intermittent strips, random or designed filamentary patterns like spirals to permit the sanitary napkin to remain breathable.

In addition, other types of fasteners can be used instead of, or in addition to adhesives. These other types of fasteners are arranged in patterns similar to those of the adhesive. Such fasteners include, but are not limited to conventional VELCRO hook material or similar fasteners.

The protective side flaps can have optional fasteners thereon for additional security. The optional protective side flap fasteners can be any of the types of fastening materials herein above. The fasteners assist the protective side flaps in staying in position after they are wrapped around the edges of the crotch surface of the protective side flaps.

Prior to use of the absorbent article the panty fastening adhesive is typically protected from contamination and from sticking to any surface where this is not desired by a protective cover means such as a silicone coated release paper, a plastic film or any other easily removable cover. The protective covermeans can be provided as a single piece or in a multitude of pieces e.g. to cover the individual adhesive areas.

Flexibility or Drapability Measurement

The procedure for measuring the flexibility/drapability of the absorbent article is as follows:

Reference

ASTM Method D1388-64: Standard Methods for Test for Stiffness of Fabrics (modified as described herein).

Principle

This test is based on the cantilever beam principle. The distance a strip of sample can be extended beyond a flat platform before it bends through a 41.5° angle is measured. The inter-action between sample weight and sample stiffness measured as the sample bends or drapes under its own weight through the given angle under specified test conditions is used to calculate the Flexibility/Drapability.

General Comments

The flexibility test is only one way of measuring a sample's flexibility and is believed to be one of the components which users of absorbent articles often refer to as softness. This measurement method should be followed as closely as possible and should not be confused with the multidirectional flexibility described in U.S. Pat. No 5,009, 653. Even so testing of samples in only the longitudinal direction is described and necessary for the present invention it is also possible for very wide or exceptionally flexible articles to measure flexibility in the transverse direction.

In general, a single sample strip should be tested only one time. The two sides of the sample should be tested on different sample strips. Likewise, sample strips for use in this test must be very carefully handled to prevent folds, wrinkles, bends, etc. This test is intended to be used on articles before they have been folded or bent for packaging by the manufacturer. If the sample is placed by the manufacturer in a folded configuration, it should be gently unfolded for the test. If only folded articles are available, the Flexibility/Drapability can be approximated by measuring a sample taken from between the fold lines. The test should be used on complete samples, i.e. with all layers having the same shape extending to the complete sample surface and fully glued together. For each sample four different strips with topsheet up and four different strips with topsheet down should be measured. Samples should be measured in longitudinal direction.

To note for relative stiff absorbent articles measurements even in longitudinal direction may not be obtainable due to the sample length being insufficient for bending through 41.5°.

| APPARATUS | |
|---|---|
| Cantilever Drape Stiffness-Tester Type SDL 003B SDL International Obtain form Carl von Gehlen/Germany (Tel.: 02168/2910; Fax 02168/24570) | |
| 1-inch Wide Cutter | Double edge cutter, 25.4 mm wide (1 inch) |
| Talcum Powder | To eliminate static charge on the tester and/or tissue. Distributed |
| Zerostat Anti-Static drape Pistol (optional) | in the USA by Discwasher, Inc., Columbia, MO 65201. May be obtained from Morgan Instruments, Inc., P.O. Box 46442, 113 Circle Freeway Dr., Cincinnati, OH 45246. Morgan Catalog No. 70-35-00. Also available from record shops and photographic supply stores. Use of this pistol is an approved way to remove static charges for this test. Never use fabric softener to remove static charge from a drape test. Operate the Anti-Static Pistol according to the manufacturer's instructions. |

Sample Preparation

The samples should be placed in an area of the room permitting maximum recirculation of air and maximising equilibration with the humidity and temperature conditions.

1. Cut 8 samples using a 1-inch wide cutter. The sample strip has to be cut lengthwise from the center of the absorbent article to be rectangular without crimp. Usual sample dimensions for measurements are 2.54 cm×14.0 cm=35.56 cm$^2$. The samples may be shorter but must comprise absorbent material throughout.
2. Remove the release paper and weight the sample (mg). Round the weight to the nearest 1 mg.
3. Carefully powder the PFA with the minimum amount of talcum sufficient to avoid sticking. Blow out the remaining talcum from the sample.
4. Weight the sample strip with talcum (mg). Round the weight to the nearest 1 mg.
5. For each sample calculate the basis weight of the sample based on weight measurement with and without talcum and the actual surface area of the sample.

6. Discard the sample if its weight increased more than 2.0 mg/cm² after adding the talcum.

Instrument Operation

Drape-tester should be placed on a bench directly in front of the operator. It is important that the bench is relatively free of vibration, that there is no air flow during the measurement and that the bench is free of draft.

The operator may either sit or stand in front of the tester while it is being used. Then the operator has to chose his position so that looking in the mirror of the tester he sees the front reference line covering the back reference line. If he sees only one line he has the right position for the measurement.

The tester shall:
1. Remove the sample slide bar from the sample slot on the top platform of the drape tester.
2. Place the sample trip on the sample slot so that one end of the strip is exactly even with the vertical edge of the tester. The strip should be placed as close as possible to the side rail of the sample slot but not touching it.
3. Place the sample slide bar on top of the sample strip so that its front edge is aligned with the edge of the sample strip in the tester and so that it touches the side rail. The sample slide bar must be carefully placed so that the sample is not wrinkled or moved forward.
4. Pulling from its free edge and using very light, gentle pressure, move the slide bar slowly and steadily forward with a speed of about 1 cm/s. As the slide bar moves forward, the sample should move at an equal slow rate. As the slide bar and the sample strip project over the edge of the tester, the sample strip will begin to bend or drape downward. Stop moving the slide bar the instant when the leading edge of the sample strip falls level with the 41.5° reference lines.

If the sample has a tendency to twist, take the reference point at the center of its leading edge. Samples which twist more than 45° cannot be measured. Samples can only be measured if the sample length is at least 0.5 cm longer than the overhang length. For non measurable samples, the overhang length can be measured only if a long enough strip can be obtained which is at least 0.5 cm longer than the overhang length.

5. Mark the overhang length on top of the sample (Overhang length:distance from the start point of movement until the point where the sample bends through 41.5°).
6. Measure the overhang length in cm with a ruler. Read the overhang length to the nearest 1 mm.

Calculation

The equation used to express Flexibility/Drapability according to the present invention is as follows:

$$G = WL^3$$

Where G equals the Flexibility/Drapability, W is the sample basis weight including talcum in milligrams/cm², and L is the length of the overhang in cm. Results are expressed in milligrams×cm or grams×cm.

Thickness Measurement

The thickness should always be measured at the thickest possible place, usually in the center of the absorbent article. For convenience the measurement is conducted on the absorbent article inclusive any protective cover means present. The article should be reconditioned at 50% humidity and 23° C. for two hours within its usual package and be removed not more than five minutes prior to the measurement.

The thickness is measured with a micrometer gauge having a range of 0 to 30 mm and capable of plus minus 0.5 mm tolerance. The gauge must not be spring loaded and should have a foot moving downwards under gravity. The micrometer foot has a diameter of 40 mm and is loaded with a 80 gram weight. The measurement is taken between 5 and 10 seconds after the foot has been lowed to come into contact with the absorbent article. Measurements should be taken often enough to allow statistical analysis to determine average thickness within a sigma of plus minus 0.1 mm. A detailed description of the thickness measurement can also be found in U.S. Pat. No. 5,009,653.

What is claimed is:

1. A flexible and breathable absorbent article for use in an undergarment, said article optionally comprising protective side flaps, said article comprising a breathable backsheet having a garment facing surface and said article comprising an absorbent core;

said garment facing surface comprising an adhesive to adhere said article to said undergarment, said adhesive having an actual adhesive surface and said adhesive defining a theoretical adhesion surface inside of an endless line which is the shortest encircling line of the adhesive without extending beyond the periphery of the garment facing surface;

said backsheet comprising an inner layer and an outer layer, said inner layer being closer to said absorbent core than said outer layer;

said article being characterized in that said outer layer comprises a hydrophobic, gas-permeable fibrous fabric layer composed of polymeric fibers;

said inner layer comprises a hydrophobic, gas-permeable polymeric film;

the surface ratio of said actual adhesive surface to said garment facing surface is in the range of 0.2 to 0.8;

the surface ratio of said theoretical adhesion surface to said garment facing surface is in the range of 0.6 to 1.0 for articles without said protective side flaps, and in the range of 0.5 to 1.0 for articles with said protective side flaps; and said article has a flexibility of 1300 mg×cm to 5000 mg×cm measured according to modify ASTM D1388.

2. An absorbent article according to claim 1 wherein said flexibility is in the range of 2000 mg×cm to 3500 mg×cm.

3. An absorbent article according to claim 2 wherein said flexibility is in the range of 2000 mg×cm to 3000 mg×cm.

4. An absorbent article according to claim 1 wherein said surface ratio of theoretical adhesion surface to said garment facing surface is in the range of 0.85 to 1.0 for articles without said protective side flaps, and in the range of 0.7 to 0.9 for articles with said protective side flaps.

5. An absorbent article according to claim 1 wherein the maximum thickness of said article along an axis perpendicular to said garment facing surface is less than 3 mm.

6. An absorbent article according to claim 5 wherein the maximum thickness of said article along an axis perpendicular to said garment facing surface is in the range of 0.5 mm to 1.5 mm.

7. An absorbent article according to claim 1 wherein said article is elastically stretchable at least in one direction parallel to said garment facing surface.

8. An absorbent article according to claim 7 wherein said article is elastically stretchable in two directions not parallel to each other but both parallel to said garment facing surface.

9. An absorbent article according to claim 1 wherein said hydrophobic, gas-permeable polymeric film is a microporous film having apertures of 200 micro meters or less, preferably 100 micro meters or less.

10. An absorbent article according to claim 9 wherein said hydrophobic, gas-permeable polymeric film is a microporous film having apertures of 100 micro meters or less.

11. An absorbent article according to claim 1 claims wherein said article is a panty liner.

12. An absorbent article according to claim 1 wherein said hydrophobic, gas-permeable polymeric film has a first liquid transport direction and a second liquid transport direction opposite said first liquid transport direction, said inner layer being oriented such that said first direction is from said outer layer towards said absorbent core, said hydrophobic, gas-permeable polymeric film allowing a liquid transport in said first liquid transport direction which is larger than the liquid transport in said second liquid transport direction.

13. An absorbent article according to claim 12 wherein said hydrophobic, gas-permeable polymeric film has apertures, said apertures being funnel shaped, said apertures having two openings positioned oppositely, one opening being larger than the other said opening.

* * * * *